(12) United States Patent
Jeong et al.

(10) Patent No.: US 9,157,802 B2
(45) Date of Patent: *Oct. 13, 2015

(54) SYSTEM FOR REAL-TIME ANALYSIS OF MATERIAL DISTRIBUTION IN CIGS THIN FILM USING LASER-INDUCED BREAKDOWN SPECTROSCOPY

(75) Inventors: Sungho Jeong, Gwangju (KR); Seokhee Lee, Gwangju (KR); Hee-Sang Shim, Gwangju (KR)

(73) Assignee: GWANGJU INSTITUTE OF SCIENCE AND TECHNOLOGY, Buk-Gu, Gwangju (KR)

( * ) Notice: Subject to any disclaimer, the term of this patent is extended or adjusted under 35 U.S.C. 154(b) by 698 days.

This patent is subject to a terminal disclaimer.

(21) Appl. No.: 13/325,840

(22) Filed: Dec. 14, 2011

(65) Prior Publication Data

US 2013/0155404 A1    Jun. 20, 2013

(51) Int. Cl.
*G01J 3/443* (2006.01)
*G01N 21/71* (2006.01)

(52) U.S. Cl.
CPC ............... *G01J 3/443* (2013.01); *G01N 21/718* (2013.01)

(58) Field of Classification Search
CPC .................. G01N 21/718; G01N 2021/8416; B23K 26/032; G01J 3/443

USPC .......................................................... 356/318
See application file for complete search history.

(56) References Cited

U.S. PATENT DOCUMENTS

| | | | | |
|---|---|---|---|---|
| 4,681,394 A | * | 7/1987 | Noguchi | 359/206.1 |
| 4,687,326 A | * | 8/1987 | Corby, Jr. | 356/5.01 |
| 4,694,164 A | * | 9/1987 | Noguchi | 250/234 |
| 6,696,008 B2 | * | 2/2004 | Brandinger | 264/400 |
| 2001/0045690 A1 | * | 11/2001 | Brandinger | 264/400 |
| 2003/0016353 A1 | * | 1/2003 | Detalle et al. | 356/318 |
| 2009/0127233 A1 | * | 5/2009 | Asano et al. | 219/121.7 |
| 2011/0100967 A1 | * | 5/2011 | Yoo et al. | 219/121.73 |

* cited by examiner

*Primary Examiner* — Kara E Geisel
(74) *Attorney, Agent, or Firm* — Nath, Goldberg & Meyer; Joshua B. Goldberg

(57) ABSTRACT

The present invention relates to a process control system which can measure the physical properties of a CIGS thin film in real-time in a continuous production line of a CIGS thin film solar cell, more specifically to a system for real-time analysis of material distribution of a CIGS thin film comprising: a header, which comprises a laser irradiation unit producing plasma from the CIGS thin film by irradiating a laser beam to a part of the CIGS thin film; and a spectrum detection optical unit detecting a spectrum generated from the plasma; a transfer unit, which transfers the header at the same rate and to the direction with the transfer rate and direction of the CIGS thin film; and a spectrum analysis unit, which analyzes the spectrum detected by the spectrum detection optical unit.

7 Claims, 11 Drawing Sheets

FIG 2

| | SIMS | AES | SEM/EDS | XRF | GD-MS | LIBS |
|---|---|---|---|---|---|---|
| Depth profiling resolution | 1-20nm | 10-100A | 0.5-3 micron | > 1 micron | 100 to 300 nm | 30 to 100 nm |
| Lateral resolution | > 10 micron | 0.01-2 micron | 0.2 to 2 micron | 10 s micron to 1 mm | > 1000 micron | 10 micron |
| Measurement time for 2 micron film | hours | hours | minutes | minutes | 10's minutes to hr | seconds |
| Detection limit | ppb | 1000 to 10000 ppm | 1000 to 10000 ppm | 100 to 1000 ppm | Sub-ppm | ppm |
| Sample preparation | Minor sectioning to put into the sample holder | Little sample prep but the sample needs to be conductive | Coating with Ir or Au | Minor palletizing or little prep | Minor surfacing cleaning or little sample prep; mainly conductive sample | Little sample prep |
| Measurement environment | High vacuum | High vacuum | High vacuum | In air | High vacuum | In air/ in chamber with buffer gas |
| Elemental coverage | Most of elements in the periodic table | Most of elements in the periodic table(except H & he) | Difficult for elements lighter than Carbon | Difficult for light elements like Na, O, N, C, B, Be, Li, etc. | Most of elements in the periodic table | Most of elements in the periodic table |
| instrument cost | 500K to 1 Mil USD | 350 to 500K USD | 500 to 750K USD (with SEM) | 80 to 150K USD | 400 to 800K USD | 120 to 170K USD |

[----------] Depth profiling for thin structure difficult
[::::::::::] Requires high vacuum and expensive instrument cost

| thickness/material | process |
|---|---|
| 3μm, Al/50 nm, Ni | E-beam evaporation |
| 10 nm, MgF | E-beam evaporation |
| 500nm, n-AZO/ 50nm, I-ZnO(BZO, GZO) | RF sputtering (or MOCVD) |
| 50nm, CdS (Cd-free ZnO, ZnS, ZnOH, In(OH)S) | CBD |
| 1~2.5 μm CIGSe(S) (or CZTS) | Co-evaporation (Sputtering +Selenization) |
| 0.5~1 μm, Mo | DC sputtering |
| 2~3 mm, Soda lime glass (SUS, Ti, Polyimide) | Cleaning |

FIG. 11
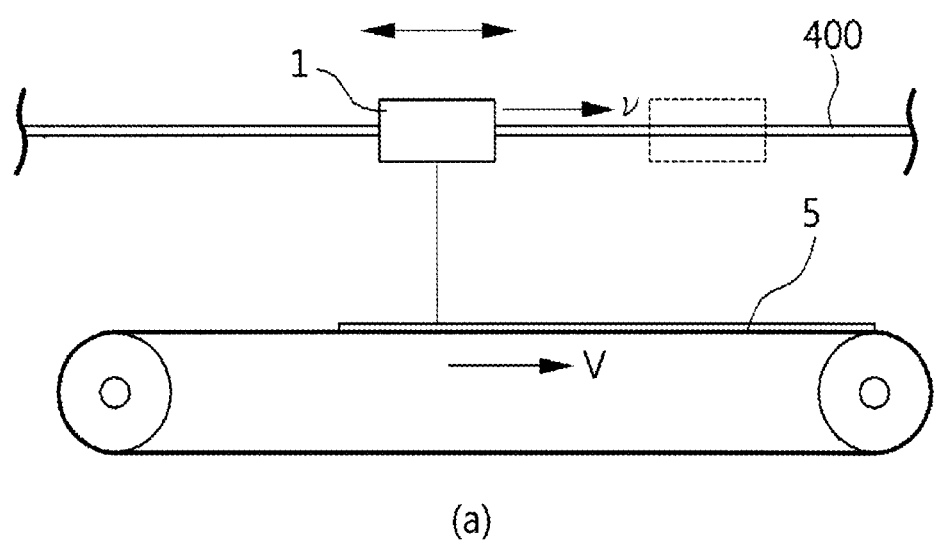
(a)
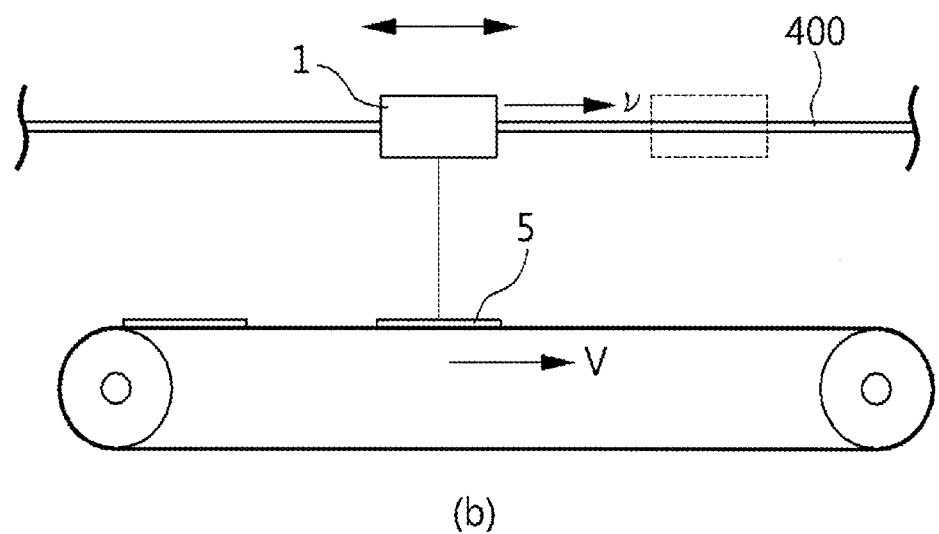
(b)

SYSTEM FOR REAL-TIME ANALYSIS OF MATERIAL DISTRIBUTION IN CIGS THIN FILM USING LASER-INDUCED BREAKDOWN SPECTROSCOPY

TECHNICAL FIELD

The present disclosure relates to a system for analysis of material distribution in a CIGS thin film, more specifically to a system for real-time analysis of material distribution in a CIGS thin film in a continuous production line of a CIGS thin film solar cell using laser-induced breakdown spectroscopy.

BACKGROUND

Plasma produced during laser irradiation emits light of certain wavelength according to a material, and therefore, constituents of the material can be qualitatively or quantitatively analyzed by collecting the light. Laser-induced breakdown spectroscopy (hereinafter, LIBS) as one of the methods analyzing constituents of a material using the collected light is a spectrum analysis technique using plasma, which is produced by causing breakdown, a kind of discharge phenomenon using high power laser, as an excitation source. A sample is evaporated in the plasma induced by laser, and atoms and ions can exist in an excited state. The excited atoms and ions emit energy after certain life, and then go back to the ground state. At this time, they emit their own wavelengths according to the kind and the excited state of the atoms. Therefore, constituents of a material can be qualitatively or quantitatively analyzed by analyzing a spectrum of the emitted wavelength.

FIG. 1 is an exemplary diagram representing the operation principle of LIBS according to the conventionally technique.

Referring FIG. 1, first of all, as shown in step (1), after the infinitesimal amount (several μg) of a material is subjected to ablation (removal of material by melting and vaporization caused by laser) by irradiating pulse laser, the ablated material is ionized within very short time (commonly, within several ns) by absorbing the laser energy so as to form plasma having high temperature of about 15000 K or more as shown in step (2). After completing laser pulse, each atom in the plasma expresses its own spectrum while the high temperature plasma is being cooled. The generated spectrum is collected using an analysis apparatus shown in step (3), and analyzed to obtain unique spectrum data of each atom. Finally, the composition and amount of the ingredients in the material can be measured by analyzing the data.

LIBS technique is distinguished from other analysis techniques in that (1) time consumed to total less than 1 sec, (2) separate sampling and pre-treatment processes are not needed for the analysis, (3) atomic constitution of the material can be analyzed with nm unit precision while ablating the material in depth because only infinitesimal amount (several μg) of material is required for one analysis, (4) separate environment is not needed for the analysis, and the analysis can be conducted in air, (5) every atoms except for inert gases can be analyzed with ppm precision, and (6) equipments can be made up at relatively low cost.

FIG. 2 is a diagram showing the result of comparing LIBS and other measuring technique.

Referring to FIG. 2, methods commonly used to measure material distribution such as SIMS (Secondary Ion Mass Spectrometry), AES (Atomic Emission Spectroscopy), EDS (Energy Dispersive X-ray Spectroscopy), GD-MS (Glow Discharge Mass Spectrometry) and the like measure the distribution only in a laboratory level but can't be actually applied to a production line because they need high vacuum. Besides, ICP-MS (Inductively Coupled Plasma-Mass Spectrometry), which is broadly being used, can't be applied to the production line because it has difficulty that a sample to be analyzed should be dissolved in a solvent before analysis. Now, XRF (X-ray Fluorescence), which is mostly used to the analysis of a solar cell material at a laboratory or site due to its convenience in use, has an advantage that the analysis can be conducted in air at relatively low cost, but has technical limits to analyze the material distribution of a CIGS thin film in that (1) it is impossible to measure the amount of Na in a CIGS thin film, which has decisive influence on the device efficiency, is impossible because analysis of light weight atoms such as Na, O, N, C, B, Be, Li and the like is almost impossible, (2) it is impossible to measure the atomic distribution in depth in a CIGS thin film having the thickness of 2 μm because the precision of XRF in depth is only about 1 μm at most, and (3) it is difficult to distinguish whether the measured fluorescence signal is from an actual thin film or from a substrate.

In general, a semiconductor solar cell is defined as a device directly converting sunlight to electricity using photovoltaic effect, wherein electrons are produced when light is irradiated to a p-n junction semiconductor diode. As the most basic constitutional elements, it is divided to three parts such as a front electrode, rear electrode and absorber layer located therebetween. Among theses, the most important material is the absorber layer, which decides most of the photoelectric conversion efficiency, and a solar cell is divided to various kinds according to the material. Particularly, when the material of the absorber layer is composed of I-III-VI$_2$ compound such as Cu(In,Ga)Se$_2$, it is called a CIGS thin film solar cell, and the CIGS thin film solar cell, a high-efficient and cheap solar cell, is receiving attention as the most firm second-generation solar cell to replace a crystalline silicon solar cell in a solar cell field where recently fierce competition is taking place all over the world, and it shows the highest efficiency of 20.6%, which is the most close efficiency to a single crystal silicon device.

FIG. 3 is an exemplary diagram schematically representing a structure of a CIGS thin film solar battery as one application area of the present invention.

FIG. 4 is a flow chart schematically representing a production process of a CIGS thin film module.

First of all, a CIGS thin film solar cell is prepared by sequentially depositing Mo layer, CIGS layer, CdS layer and TCO layer on a substrate, and it is more specifically prepared in detail as follows. The CIGS thin film module is prepared by, first of all, depositing Mo as a rear electrode layer on a substrate; forming a pattern by a scribing process (P1 scribing); sequentially depositing CIGS layer as an absorber layer and CdS buffer layer on the pattern-formed Mo layer; forming a pattern by a scribing process (P2 scribing); depositing again TCO (transparent conductive oxide) layer on the CdS layer followed by depositing a front electrode grid of Ni/Al; and then finally proceeding a scribing process to form a pattern (P3 scribing). The said scribing process is a patterning process to serially connect the patterns at regular intervals in order to prevent the efficiency reduction caused by increase of the sheet resistance with increased area of the solar cell, and the process is conducted via three times of P1, P2 and P3. Conventionally, the P1 scribing was patterned by laser, and the P2 and P3 scribing were patterned by a mechanical method, but recently, a method using laser to pattern all of the P1, P2 and P3 scribing is being developed.

In case of this CIGS thin film solar cell, it is being reported that not only the thickness of the thin film (1~2.2 μm) or the device structure but also the composition of the constituent material of the CIGS thin film as a multi-component compound and atomic distribution in the thin film have critical influence on the light absorption rate and photoelectric conversion efficiency. Further, it is being reported that Na, which is diffused from a soda-lime glass largely used as a substrate to a CIGS absorber layer during a process, increases the photoelectric conversion efficiency by increasing the electric charge concentration of the thin film (Nakada et al., Jpn. J. Appl. Phys., 36, 732 (1997)), or by increasing the grain size of the CIGS single crystal so as to reduce the structural characteristic change according to the composition change (Rockett et al., Thin Solid Films 361-362 (2000); Probst et al., Proc. of the First World Conf. on Photovoltaic Energy, Conversion (IEEE, New York, 1994), p. 144). These reports suggest that the chemical property of the absorber layer should be controlled through the distribution analysis of a material in the thin film for quality control at the CIGS thin film solar cell production line.

On the other hand, the continuous production process of the CIGS thin film solar cell is largely divided to a Roll-to-Plate (hereinafter, R2P) process using a hard material substrate such as a soda-lime glass, and a Roll-to-Roll (hereinafter, R2R) process using a soft material substrate such as metal thin plate (e.x., stainless steel, Ti, Mo, Cu and the like) or polymer (e.x., polyimide). Now, the physicochemical property should depend on the previously decided value in the research and development step because a system, which can analyze the physicochemical properties of the CIGS thin film having strong influence on the product performance in real-time, is not equipped yet in these continuous production lines. Further, it is impossible to check separately even if the property is out of the physicochemical standard desired in the actual production process, and therefore, the error should be found out through the decrease of the performance and quality in the evaluation step of the finally completed product, and great product loss is generated. Because many efforts and time are consumed to find out physicochemical variables causing falling off in product performance and quality in the said continuous production process, cost increase and falling off in competitiveness are caused consequently. Therefore, development of a process control system, which can analyze the physicochemical properties of a produced CIGS thin film in real-time in the continuous production process line without a pre-treatment process, is desperately needed.

SUMMARY

One object of the present invention is to provide a process control system which can measure the physical properties of a CIGS thin film in real-time in a continuous production line of a CIGS thin film solar cell.

In order to achieve the object of the present invention, provided is a system for real-time analysis of material distribution of a CIGS thin film comprising:

a header, which comprises a laser irradiation unit producing plasma from the CIGS thin film by irradiating a laser beam to a part of the CIGS thin film; and a spectrum detection optical unit detecting a spectrum generated from the plasma;

a transfer unit, which transfers the header at the same rate and to the direction with the transfer rate and direction of the CIGS thin film by being bound to the upper part of the header; and a spectrum analysis unit, which analyzes the spectrum detected by the spectrum detection optical unit by being electrically connected with the spectrum detection optical unit.

BRIEF DESCRIPTION OF THE DRAWINGS

FIG. 2 is a diagram showing the result of comparing LIBS and other measuring technique.

FIG. 11 is an exemplary diagram illustrating one example of the real-time analysis system of the CIGS thin film material distribution according to the present invention applied to (a) R2R and (b) R2P continuous production processes.

DESCRIPTION OF SYMBOLS

Figure 1:
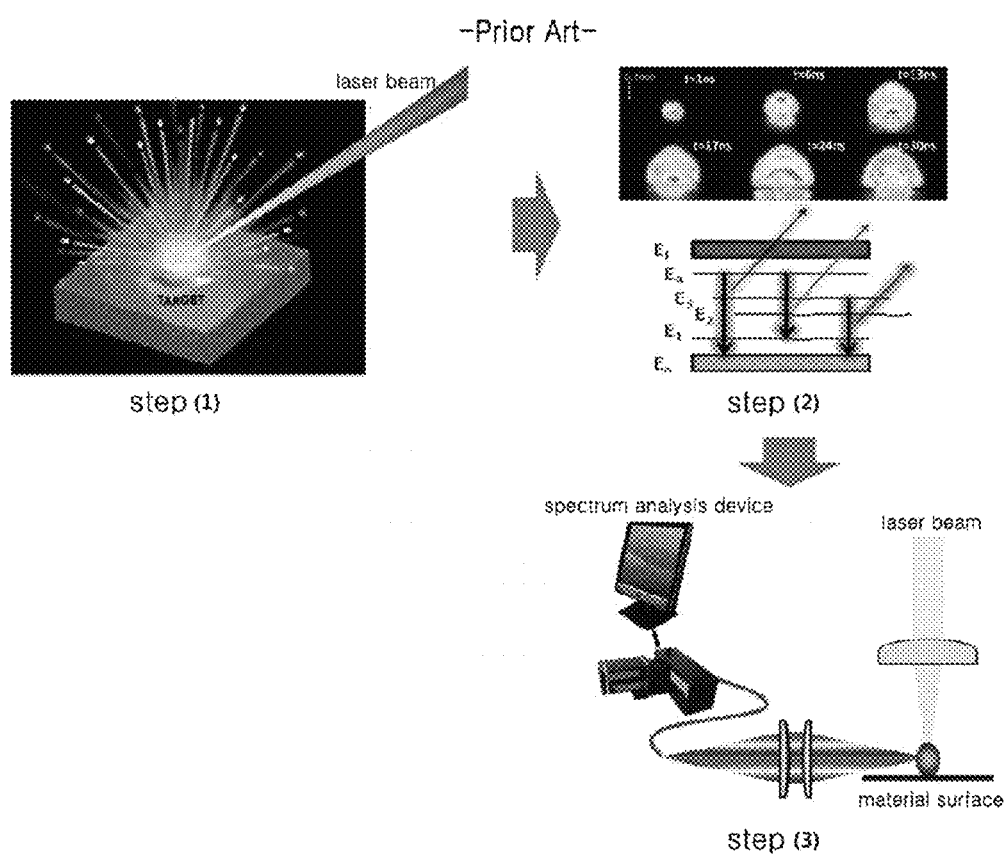
FIG. 1 is an exemplary diagram representing the operation principle of LIBS.
Figure 3:
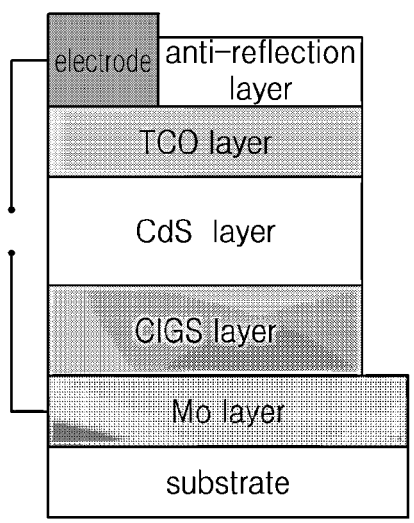
FIG. 3 is an exemplary diagram schematically representing a structure of a CIGS thin film solar battery.
Figure 4:
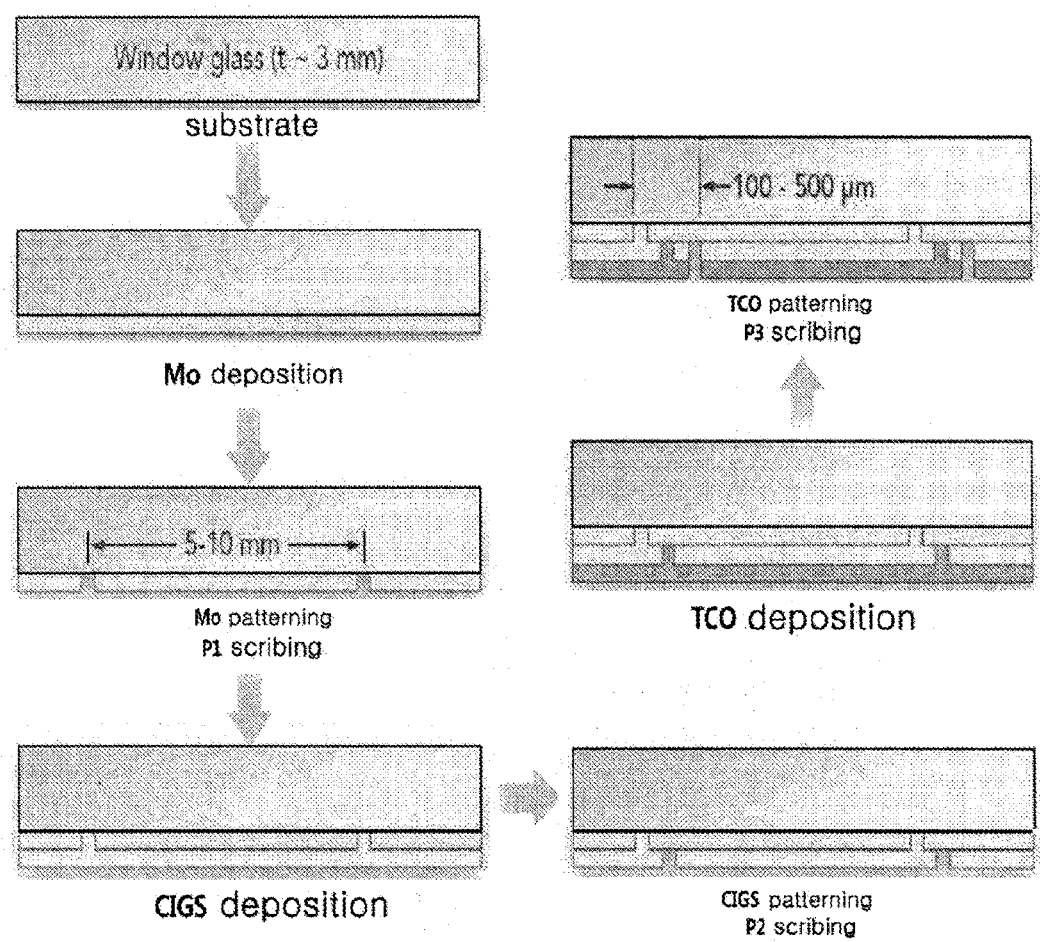
FIG. 4 is a flow chart representing a schematic production process of a CIGS thin film solar battery.

1: a real-time analysis system of the CIGS thin film material distribution
5: thin film
100: header 200: header transfer unit
300: spectrum analysis unit 400: header transfer route
500: platform
10: laser irradiation unit 20: spectrum detection optical unit
30: beam irradiation position adjustment unit 40: indicator recognition optical unit
110: laser unit 120: automatic focusing unit
D: thin film transfer direction V: thin film transfer rate
d: header transfer unit transfer direction v: header transfer unit transfer rate

DETAILED DESCRIPTION

Hereinafter, preferred embodiments of the present invention will be described in detail with reference to the accompanying drawings. However, the present invention is not limited to the examples described herein, and may contain other equivalents or substitutes. In drawings, thickness of layers and regions are exaggerated for clarity. Throughout the entire specification, the same symbols represent the same elements, and detailed descriptions of functions or constitutions known in the art may be omitted to avoid obscuring the subject matter of the present invention.

Figure 5:
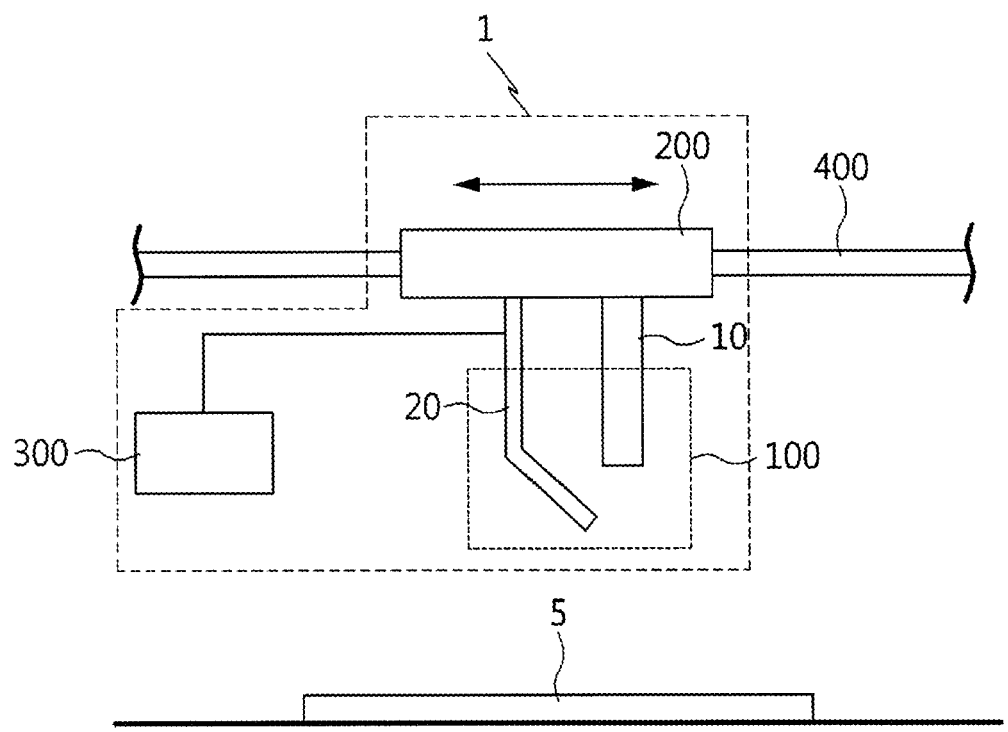
FIG. 5 is an exemplary diagram illustrating a real-time analysis system of the CIGS thin film material distribution according to one embodiment of the present invention.

FIG. 5 is an exemplary diagram illustrating a real-time analysis system of the CIGS thin film material distribution according to one embodiment of the present invention.

Referring to FIG. 5, the real-time analysis system of a CIGS thin film material distribution (1) of the present invention comprises a header (100), a header transfer unit (200) and a spectrum analysis unit (300). The upper part of the header (100) is bound to the header transfer unit (200), irradiates a laser beam to a CIGS thin film (5), and detects a spectrum of the plasma generated from the CIGS thin film (5). Further, the header transfer unit (200) transfers the header (100) in combination with the transfer of the CIGS thin film (5). Therefore, the header (100) is transferred in combination with the CIGS thin film (5) according to the transfer of the header transfer unit (200). Further, the spectrum analysis unit (300) analyzes spectrum information transferred from the header (100), and senses whether the chemical or physical distribution of the material making up the CIGS thin film (5) is normal or not.

First of all, the header (100) consists of a laser irradiation unit (10) and a spectrum detection optical unit (20).

The laser irradiation unit (10) is connected to the header transfer unit (200), and a certain laser is irradiated to the CIGS thin film (5). Kinds of the laser beam being output from the laser irradiation unit (10) can be properly selected by a skilled person in the art according to the characteristic of the produced CIGS thin film (5). The plasma is generated from the CIGS thin film (5) by the irradiation of the laser beam through the laser irradiation unit (10). Particularly, it is preferred that the laser beam irradiated according to the quality of the material and chemical composition of the CIGS thin film (5) is properly selected to make the ablation of the CIGS thin film (5) easy.

The spectrum detection optical unit (20) is connected to the header transfer unit (200), and arranged to the position adjacent to the laser irradiation unit (10). Particularly, it is preferred to be arranged to the proper position to sense the spectrum component of the plasma generated from the CIGS thin film (5).

The header transfer unit (200) is transferred in combination with the transfer of the CIGS thin film. For example, when the CIGS thin film (5) is horizontally transferred to the certain direction, the header (100) is arranged to the upper part of the CIGS thin film (5) to continuously irradiate the laser beam to the same position of the CIGS thin film (5) being transferred and to detect the spectrum while transferring the header transfer unit (200) to the same rate (V) and direction (D) with those of the CIGS thin film (5).

The spectrum analysis unit (300) is connected to the header (100). More specifically, it is electrically connected to the spectrum detection optical unit (20) making up the header (100) to analyze the spectrum sensed at the spectrum detection optical unit (20). For example, when the spectrum sensed at the spectrum detection optical unit (20) comprises an unique LIBS intensity information according to a material making up the CIGS thin film (5), the spectrum analysis unit (300) analyzes the information, understand the ratio and distribution of the components of the CIGS thin film (5), and judge whether the chemical composition or physical distribution of the produced CIGS thin film (5) has error or suitability.

Figure 6:
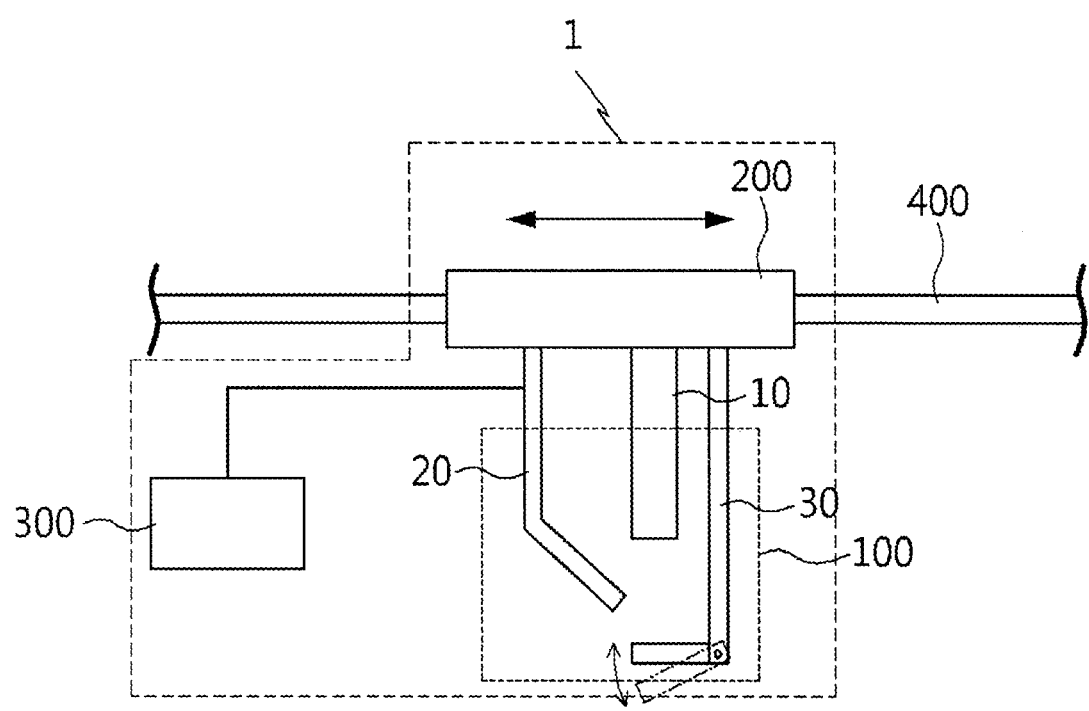
FIG. 6 is an exemplary diagram illustrating a system further comprising a beam irradiation position adjustment unit in addition to the real-time analysis system of the CIGS thin film material distribution according to one embodiment of the present invention.

FIG. 6 is an exemplary diagram illustrating a system further comprising a beam irradiation position adjustment unit in addition to the real-time analysis system of the CIGS thin film material distribution according to one embodiment of the present invention.

Referring FIG. 6, the real-time analysis system of the CIGS thin film material distribution shown in FIG. 6 has the same constitutional factors with the system disclosed in the FIG. 5, and the beam irradiation position adjustment unit (30) is further added to the header (100).

The beam irradiation position adjustment unit (30) minutely adjusts the position where the laser beam is irradiated to the CIGS thin film (5) under the condition that the laser irradiation unit (10) is fixed to the header transfer unit (200). Namely, the irradiation position of the laser beam is primary set according to the transfer of the header transfer unit (200). Further, when fine adjustment of the irradiation position is needed at the position where the header transfer unit (200) is set, the beam irradiation position adjustment unit (30) can control the irradiation position of the laser beam by adjusting the reflection angle of the irradiated laser beam.

For example, in FIG. 6, in the beam irradiation position adjustment unit (30) arranged to the form of "⌐", a part horizontal to the header transfer unit (200) is made up of a reflection mirror, and the irradiation position of the laser beam can be controlled by adjusting the angle of the reflection mirror. In FIG. 6 expressing the real-time analysis system of the CIGS thin film material distribution as a side view, it is only expressed that the reflection mirror horizontal to the header transfer unit (200) can move up and down, but the reflection mirror can also move from front to back and side to side on the side view. The irradiation position of the laser beam can be secondarily controlled by introducing the beam irradiation position adjustment unit (30) of various means, and particularly, the beam irradiation position adjustment unit (30) may be a "galvanometer" generally used in the art.

Figure 7:
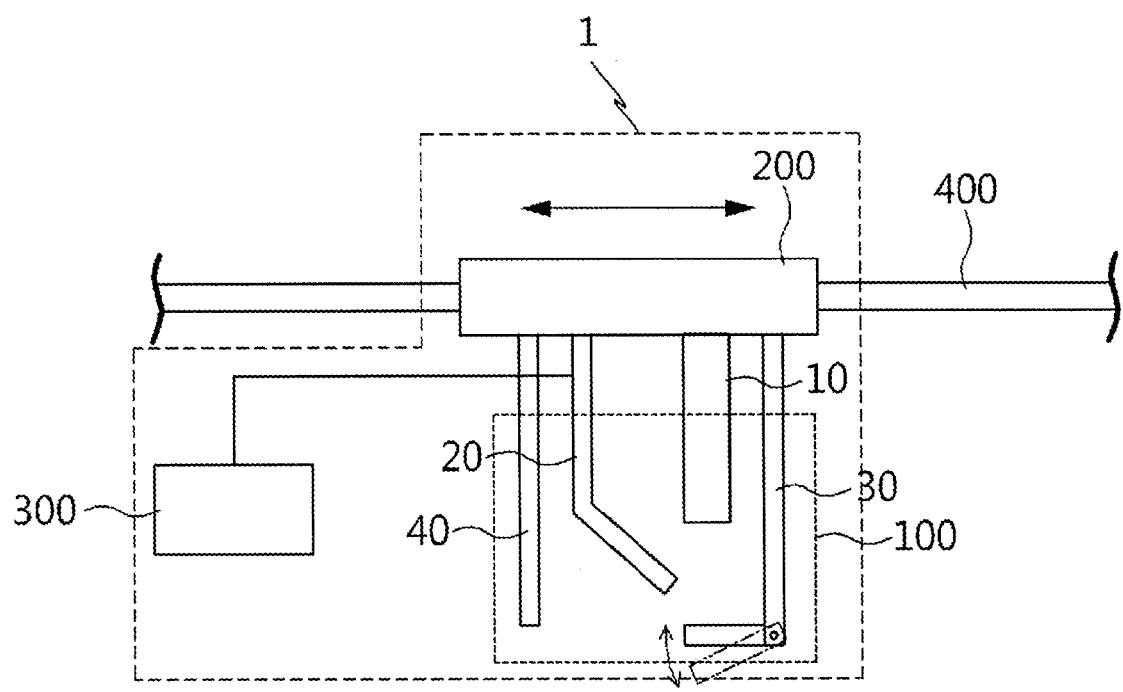
FIG. 7 is an exemplary diagram illustrating a system further comprising an indicator recognition optical unit in addition to the real-time analysis system of the CIGS thin film material distribution according to one embodiment of the present invention.

FIG. 7 is an exemplary diagram illustrating a system further comprising an indicator recognition optical unit in addition to the real-time analysis system of the CIGS thin film material distribution according to one embodiment of the present invention.

Referring FIG. 7, the real-time analysis system of the CIGS thin film material distribution shown in FIG. 7 has the same constitutional factors with the system disclosed in the FIG. 5, and the indicator recognition optical unit (40) is further added to the header (100). Therefore, the descriptions of the constitutional factors which are same with those of the FIG. 5 or 6 are omitted and the added indicator recognition optical unit is described as follow.

The indicator recognition optical unit (40) is connected to the header transfer unit (200). The indicator recognition optical unit (40) may be a factor called 'vision' in the art. Namely, the surface image of the CIGS thin film (5) is taken under the condition that the image of the CIGS thin film (5) is captured or saved, and compared with the previously saved surface image of the CIGS thin film (5) to determine the position where to laser beam is irradiated. The irradiation position of the laser beam in the CIGS thin film (5) can be determined by introducing the indicator recognition optical unit (40) of various means, and therefore, a user can irradiate the laser beam to the desired position.

Figure 8:
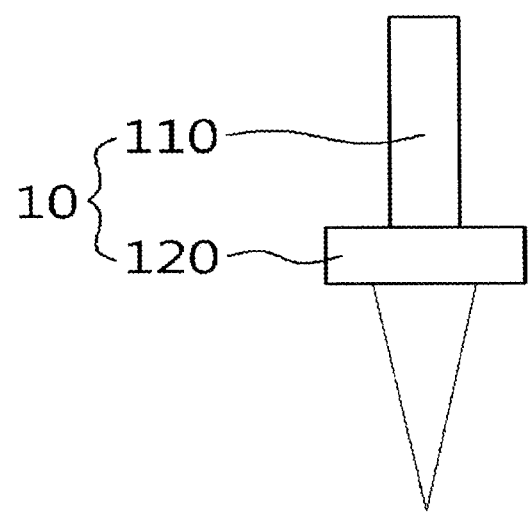
FIG. 8 is an exemplary diagram more specifically illustrating the laser irradiation unit illustrated in FIGS. 5 to 7 in the real-time analysis system of the CIGS thin film material distribution according to one embodiment of the present invention.

FIG. 8 is an exemplary diagram more specifically illustrating the laser irradiation unit illustrated in FIGS. 5 to 7 in the real-time analysis system of the CIGS thin film material distribution according to one embodiment of the present invention.

Referring FIG. 8, the laser irradiation unit (10) is making up of a laser unit (110) and an automatic focusing unit (120).

The laser unit (110) produces a laser beam, or transfers the produced laser beam to the automatic focusing unit (120). Particularly, in the laser unit (110) all kinds of laser, which can ablate the CIGS thin film (5), can be used, but it is preferred to use any one laser selected from a group consisting of ND:YAG laser, Nd:YLF laser and ND:YV04 laser in the laser unit (110). Particularly, ND:YAG laser can be used in the laser unit (110).

Further, the automatic focusing unit (120) adjusts a focus of the laser beam supplied from the laser unit (110). Particularly, the focus of the laser beam can be automatically adjusted through the automatic focusing unit (120). For this, a separate sensing device, which can sense the focus of the laser beam but not illustrated in FIGS. 5 to 8, is equipped thereto, and the automatic focusing unit (120) can adjust the focus of the laser beam by using the focus information delivered through the device.

Further, the irradiation position of the laser beam can be adjusted not only to the same direction with the CIGS thin film (M) transfer direction (D) but also within a range of −180° to +180° on the basis of the transfer direction of the CIGS thin film (D) by adjusting the angle of the reflection mirror of the beam irradiation position adjustment unit (30) disclosed in FIGS. 6 and 7.

Figure 9:
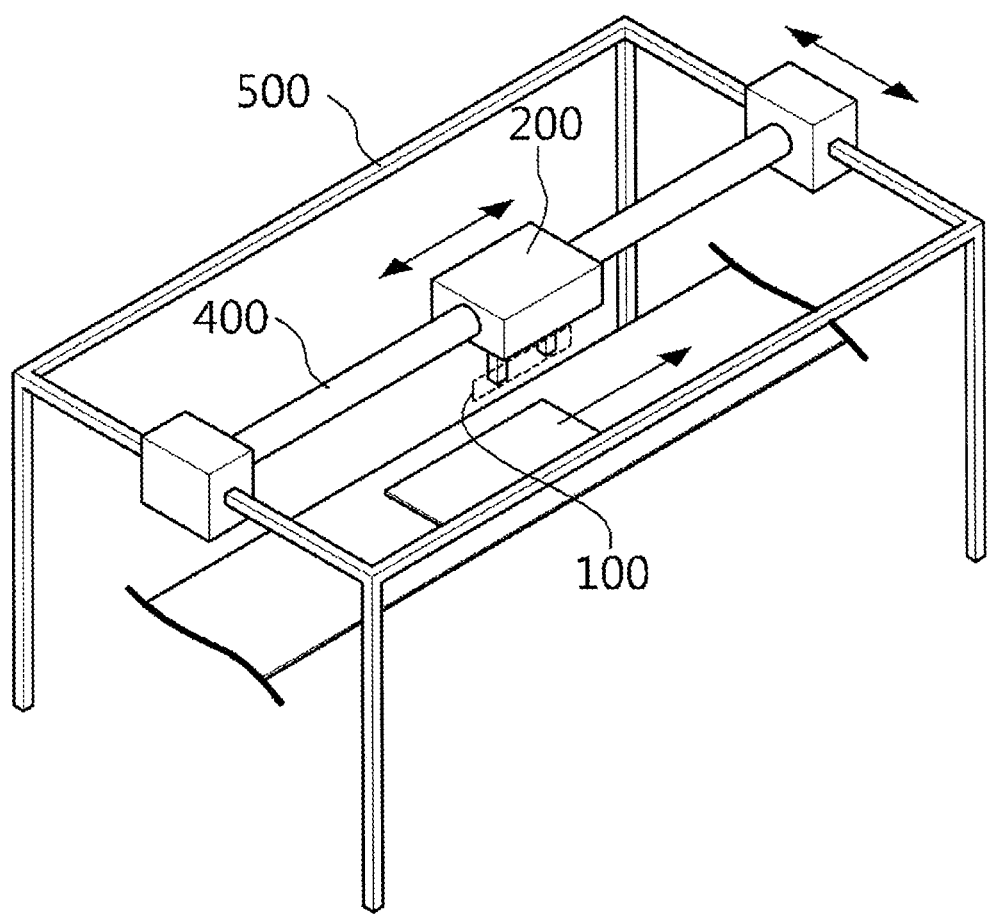
FIG. 9 is an exemplary diagram to explain the operations of the header and the header transfer unit in the real-time analysis system of the CIGS thin film material distribution according to the present invention.

FIG. 9 is an exemplary diagram to explain the operations of the header and the header transfer unit in the real-time analysis system of the CIGS thin film material distribution according to the present invention.

Referring FIG. 9, the header transfer unit (200) transfers the header (100) to the same direction (d) with the CIGS thin film (5) transfer direction (D) at the same rate (v) with the CIGS thin film (5) transfer rate (V). Therefore, the constituents of the header (100) such as the laser irradiation unit (10), the spectrum detection optical unit (20) and the like transfer to the same direction at the same rate with the CIGS thin film (5) transfer rate (V) and direction.

The header transfer unit (200) is transferred along a header transfer route (400), which is formed to the same direction with the CIGS thin film (5) transfer direction (D) at a fixed platform (500). The header transfer route (400) can move perpendicularly to the CIGS thin film (5) transfer direction (D) on the fixed platform (500), and also the header (100) can move perpendicularly to the direction with the CIGS thin film (5) transfer direction (D) as the header transfer route (400) moves to the perpendicular direction to the CIGS thin film (5) transfer direction (D). Namely, the position where the laser beam is irradiated from the laser irradiation unit (10) can be globally positioned according to the header transfer unit (200), and the header transfer route (400) which can move to the perpendicular direction to the CIGS thin film (5) transfer direction (D).

Figure 10:
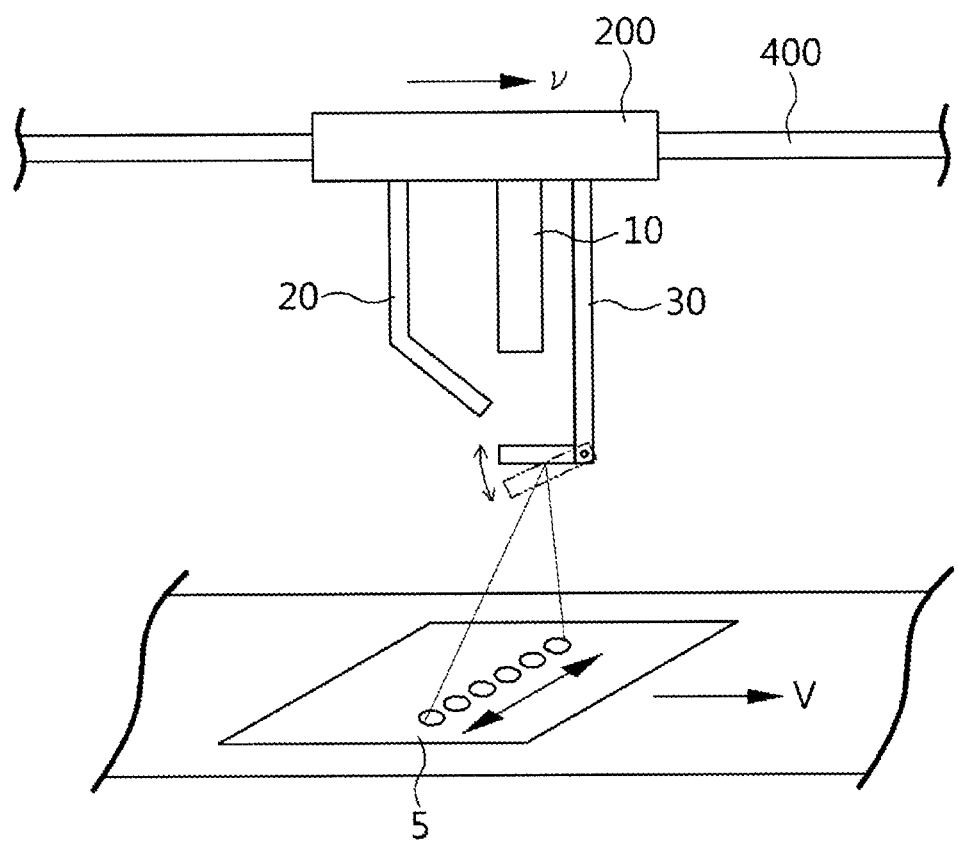
FIG. 10 is an exemplary diagram illustrating the principle that the laser beam irradiation position is minutely adjusted by the beam irradiation position adjustment unit in one embodiment of the present invention.

FIG. 10 is an exemplary diagram illustrating the principle that the laser beam irradiation position is minutely adjusted by the beam irradiation position adjustment unit in one embodiment of the present invention.

Referring FIG. 10, the position can be adjusted not only to the same direction with the CIGS thin film (M) transfer direction (D) but also within a range of −180° to +180° on the basis of the transfer direction of the CIGS thin film (D) by adjusting the angle of the reflection mirror of the beam irradiation position adjustment unit (30). Although FIG. 10 only shows that it can be adjusted to the −90° 및 90° direction on the basis of the CIGS thin film transfer direction (D), but not limited thereto.

FIG. 11 is an exemplary diagram illustrating one example of the real-time analysis system of the CIGS thin film material distribution according to the present invention applied to (a) R2R and (b) R2P continuous production processes.

Referring FIG. 11, the real-time analysis system of the CIGS thin film material distribution (S) can be applied to the R2R or R2P process as the CIGS continuous production process. The kind of the process may differ according to the kind of substrates used to the production of the CIGS thin film (5). The real-time analysis system of the CIGS thin film material distribution (S) can be applied to the R2P process when the CIGS thin film (5) uses a substrate of hard material such as a soda-lime glass. On the other hand, the real-time analysis system of the CIGS thin film material distribution (S) can be applied to the R2R process when the CIGS thin film (5) uses a substrate of soft material such as a metal thin plate (e.x., stainless steel, Ti, Mo, Cu and the like) or polymer (e.x., polyimide).

The system of the present invention can analyze material distribution of a CIGS thin film in real-time in a continuous production process of the CIGS thin film solar cell so as to analyze the physicochemical properties of the CIGS thin film more accurately and precisely as well as rapidly. Therefore, it can save efforts and time consumed to evaluate the product performance and quality, and can be usefully used to efficiently produce a CIGS thin film solar cell with constant quality.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A system for real-time analysis of material distribution of a CIGS thin film in a continuous production line being transferred in a direction D at a rate V comprising:
    a header, which comprises a laser irradiation unit positioned above the CIGS thin film that produces plasma by irradiating a laser beam to a part of the CIGS thin film; and a spectrum detector configured to detect a spectrum generated from the plasma;
    a transferer configured to transfer the header in the direction D at the rate V with the CIGS thin film being transferred such that the part of the CIGS thin film is continuously irradiated by the laser beam; and
    a spectrum analyzer electrically connected with the spectrum detection optical unit and configured to analyze the detected spectrum.

2. The system of claim 1, wherein the laser irradiation unit comprises a laser and an automatic focuser configured to adjust focus of the laser beam supplied from the laser.

3. The system of claim 1, wherein the header further comprises a beam irradiation position adjustment unit configured to control an irradiation position of the laser beam.

4. The system of claim 3, wherein the beam irradiation position adjustment unit is a galvanometer.

5. The system of claim 3, wherein the irradiation position of the laser beam is within a range of −180° to +180° relative to direction D.

6. The system of claim 1, wherein the header further comprises an optical recognition indicator configured to capture or save a surface image of the CIGS thin film and compare the surface image with a previously saved surface image to determine where the laser beam is to be irradiated.

7. A process control system for real-time analysis of material distribution of a CIGS thin film in a continuous production line being transferred in a direction D at a rate V comprising:

a header comprising a laser irradiation unit positioned above the CIGS thin film, which produces plasma by irradiating a laser beam to a part of the CIGS thin film, and a spectrum detector configured to detect a spectrum generated from the plasma;

a transferer configured to transfer the header in the direction D at the rate V with the CIGS thin film being transferred such that the part of the CIGS thin film is continuously irradiated by the laser beam; and a spectrum analyzer electrically connected with the spectrum detector and configured to analyze the detected spectrum, wherein the continuous production line is a roll-to-plate (R2P) or a roll-to-roll (R2R) process.

* * * * *